(12) United States Patent
White et al.

(10) Patent No.: US 10,825,314 B2
(45) Date of Patent: Nov. 3, 2020

(54) BABY MONITOR

(71) Applicant: EGW Technologies LLC, Woodbridge, NJ (US)

(72) Inventors: Eric Gregory White, Tinton Falls, NJ (US); David Robert Abrams, Aberdeen, NJ (US)

(73) Assignee: MiKu, Inc., Woodbridge, NJ (US)

( * ) Notice: Subject to any disclaimer, the term of this patent is extended or adjusted under 35 U.S.C. 154(b) by 67 days.

(21) Appl. No.: 15/658,285

(22) Filed: Jul. 24, 2017

(65) Prior Publication Data

US 2018/0053393 A1 Feb. 22, 2018

Related U.S. Application Data

(60) Provisional application No. 62/377,035, filed on Aug. 19, 2016.

(51) Int. Cl.
| | | |
|---|---|---|
| G08B 21/02 | (2006.01) | |
| G06T 7/00 | (2017.01) | |
| G06T 7/20 | (2017.01) | |
| H04N 5/232 | (2006.01) | |
| H04N 5/33 | (2006.01) | |
| A61B 5/00 | (2006.01) | |
| A61B 5/11 | (2006.01) | |
| A61B 7/00 | (2006.01) | |

(Continued)

(52) U.S. Cl.
CPC ........ *G08B 21/0208* (2013.01); *A61B 5/0077* (2013.01); *A61B 5/1128* (2013.01); *A61B 5/725* (2013.01); *A61B 5/7264* (2013.01); *A61B 5/7278* (2013.01); *A61B 5/742* (2013.01); *A61B 7/00* (2013.01); *G06T 7/0016* (2013.01); *G06T 7/20* (2013.01); *H04N 5/23293* (2013.01); *H04N 5/33* (2013.01); *A61B 2503/04* (2013.01); *A61B 2576/00* (2013.01); *G06T 2207/10024* (2013.01); *G06T 2207/10028* (2013.01); *G06T 2207/10048* (2013.01); *G06T 2207/30076* (2013.01)

(58) Field of Classification Search
CPC combination set(s) only.
See application file for complete search history.

(56) References Cited

U.S. PATENT DOCUMENTS

| | | | |
|---|---|---|---|
| 5,652,570 A * | 7/1997 | Lepkofker | ............ A61B 5/1112 |
| | | | 340/573.4 |
| 7,403,638 B2 | 7/2008 | Jeung et al. | |

(Continued)

FOREIGN PATENT DOCUMENTS

JP 2004-537335 12/2004

*Primary Examiner* — Alexander Gee
(74) *Attorney, Agent, or Firm* — LaMorte & Associates P.C.

(57) ABSTRACT

Systems and methods are described herein for monitoring and capturing information associated with target subjects, such as babies. For example, the systems and methods provide a capture device, such as a camera, that captures capture time of flight (TOF) data from a target subject. Using the TOF data, the systems and methods, via a display device associated with (e.g., paired to) the capture device, present information about the target subject, such as information indicating movement of the target subject, information indicating a breathing rate of the target subject, information indicating a heart rate of the target subject, and so on.

8 Claims, 9 Drawing Sheets

(51) Int. Cl.
 *G16H 50/20* (2018.01)
 *G16H 30/40* (2018.01)

(56) References Cited

U.S. PATENT DOCUMENTS

| | | | |
|---|---|---|---|
| 9,311,715 B2 | 4/2016 | Rafii et al. | |
| 2009/0207426 A1* | 8/2009 | Zandifar | G06T 7/0004 |
| | | | 358/1.9 |
| 2009/0304270 A1* | 12/2009 | Bhagavathy | G06T 5/002 |
| | | | 382/162 |
| 2010/0217763 A1* | 8/2010 | Park | H04B 7/0413 |
| | | | 707/737 |
| 2013/0057654 A1* | 3/2013 | Rafii | G06K 9/00201 |
| | | | 348/46 |
| 2014/0142729 A1 | 5/2014 | Lobb et al. | |
| 2015/0054975 A1* | 2/2015 | Emmett | H04N 5/23245 |
| | | | 348/220.1 |
| 2015/0087997 A1* | 3/2015 | Haider | A61B 5/0077 |
| | | | 600/474 |
| 2016/0035037 A1* | 2/2016 | Bulan | G06K 9/3258 |
| | | | 705/4 |
| 2016/0094812 A1 | 3/2016 | Chen | |
| 2016/0232684 A1* | 8/2016 | Kholodenko | H04N 13/204 |
| 2017/0055877 A1* | 3/2017 | Niemeyer | A61B 5/0077 |

\* cited by examiner

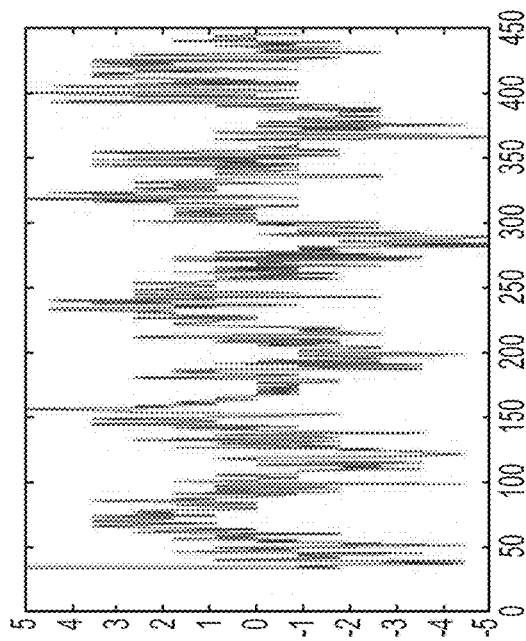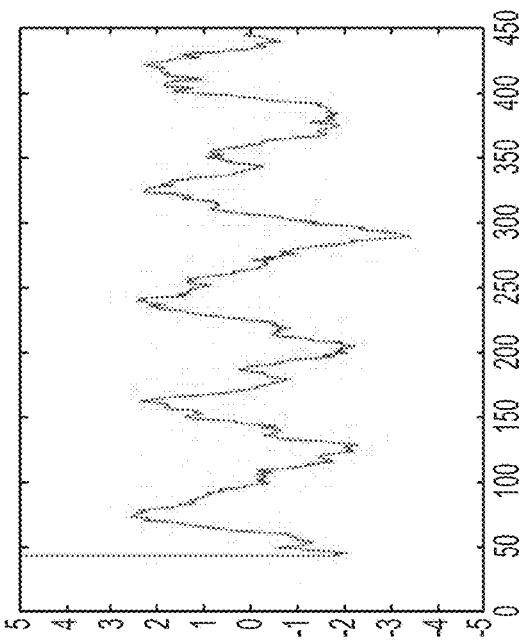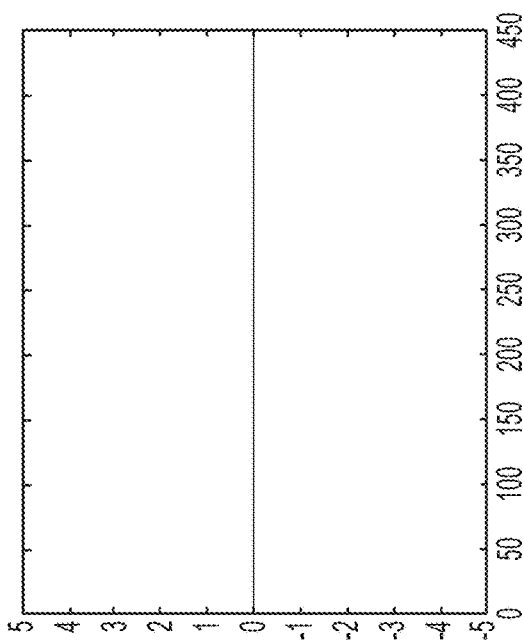

BABY MONITOR

CROSS REFERENCE TO RELATED APPLICATIONS

This application claims priority to U.S. Provisional Patent Application No. 62/377,035 filed on Aug. 19, 2016, entitled Baby Monitor, which is hereby incorporated by reference in its entirety.

BACKGROUND

Conventional baby monitors are very simple in operation—they capture sounds and/or images of a baby (or other target subject), such as a baby sleeping in a crib, and relay the captured sounds/images to a remote device, which presents an audio or video feeds of the baby to a parent or other user of the remote device. The parent, using the baby monitor, is able to hear or view their baby, but receives little more information regarding the health or physical state of their child.

Recently, baby monitors have been developed that attempt to capture and present more granular or specific data about a monitored baby. For example, wearable sensors have been configured to monitor the movement of the baby, the heart rate of the baby, the breathing of the baby, and so on. However, such sensors, which may be integrated into a baby's clothing or attached to the baby in wearable devices, have various limitations. For example, additional devices require additional management and care, and may irritate or make a baby physically uncomfortable. Also, they often capture false or inaccurate readings, providing unreliable data regarding the characteristics they are deployed to monitor. Most recently, image-processing based solutions have emerged in the market that extract breathing and heart rate from a video feed of the sleeping baby. These solutions suffer in situations where video footage is non-ideal, erroneous, inconsistent, etc. These image-processing solutions often require internet connectivity for cloud processing. This is a limitation since the system will not work if Internet goes down as well as adding additional latency.

SUMMARY

Example embodiments and implementations of the inventions described herein are directed to systems and methods of capturing and processing images to determine various parameters and conditions associated with the subject or object captured by the imaging system.

In one example embodiment, an imaging system comprises a capture device that monitors a subject, the capture device includes: one or more infrared light components; an infrared sensor that captures infrared measurements for the monitored subject; a time of flight (TOF) sensor that captures TOF data for the monitored subject; and a movement determination module that determines a state of movement of the monitored subject based on the TOF data for the monitored subject that is captured by the TOF sensor.

In another example embodiment the imaging system also comprises a display device that displays a visual image of the monitored subject based on data received from the capture device, the display device includes: an indication module that causes the display device to: present a first indicator associated with movement of the monitored subject; and present a second indicator associated with respiration of the monitored subject.

Further example embodiments of the present invention may include one or more of the following features. The TOF sensor captures depth images associated with the monitored subject that include pixels representing distances to one or more areas of the monitored subject. The TOF sensor captures depth images associated with a torso of the monitored subject. The TOF sensor captures depth images associated with one or more limbs of the monitored subject. The capture device includes a stand configured to position the TOF sensor proximate to the monitored subject or a mount configured to attach the capture device to furniture, such as a crib, that is proximate to the monitored subject. The capture device further includes an RGB camera configured to capture RGB images of the monitored subject; and/or a microphone configured to capture audio data associated with the monitored baby.

In yet another example embodiment of the present invention a system for presenting images of a monitored subject, such as an infant, comprises a display module, a movement determination module, and an indication module. The display module causes a user interface associated with the system to present a visual image of the monitored subject based on RGB data and/or infrared data captured by one or more image sensors proximate to the monitored subject. The movement determination module determines a state of movement of the monitored subject based on TOF data for the monitored subject that is captured by a TOF sensor proximate to the monitored subject. And an indication module causes the user interface to present a first indicator associated with movement of the monitored subject based on the determined state of movement of the monitored subject and present a second indicator associated with respiration or heart rate of the monitored subject based on the determined state of movement of the monitored subject.

Further example embodiments of the present invention may include one or more of the following features. The display module is part of a stand-alone display device that is communicatively paired to a capture device that is positioned proximate to the monitored subject and includes the movement determination module. The display module is part of a mobile device that receives data from a capture device that is positioned proximate to the monitored subject and includes the movement determination module. The TOF data includes depth images associated with the monitored subject that include pixels representing distances to one or more areas of the monitored subject. The indication module presents the first indicator associated with movement of the monitored subject over an image of an area of the monitored subject determined to be moving based on the determined state of movement. The indication module presents the second indicator associated with respiration or heart rate of the monitored subject over an image of a torso of the monitored subject when the monitored subject is determined to be breathing based on the determined state of movement. The indication module further presents a third indicator associated with a heart rate of the monitored baby based on the determined state of movement of the monitored baby. The movement determination module determines the state of movement of the monitored subject based on determining pixel velocities for one or more areas of the monitored subject that are based on the TOF data.

A further still example embodiment of the present invention may also an alert module that invokes an alert when the determined state of movement falls outside a threshold range of values associated with a suitable breathing rate for the monitored subject. The alert module invokes an alert when the determined state of movement falls outside a threshold range of values associated with movement of the monitored subject.

An additional example embodiment of the present invention includes a method performed by a monitoring system comprising the steps of: receiving depth image data from a depth image sensor proximate to a target subject; and determining a movement status, breathing status, and/or heart rate of the target subject based on the received depth image data.

Further example embodiments of the present invention may include one or more of the following features, steps, or functions. The received depth image data includes time of flight (TOF) depth images associated with the target subject that includes pixels representing distances to one or more areas of the target subject. Determining a movement status, breathing status, and/or heart rate of the target subject based on the received depth image data includes determining pixel velocities for pixels representing one or more areas of the target subject that are based on the depth image data.

In yet another example embodiment of the present invention a monitoring method, comprises the steps of: receiving time of flight (TOF) data measured from a target subject; parsing the TOF data to extract a phase frame and an amplitude frame from the TOF data; determining pixel velocities for pixels from distance data of the phase frame; down-selecting high confidence pixels using a mask generated from confidence data of the amplitude frame; filtering the high confidence pixels; thresholding the filtered high confidence pixels; for each frame, performing blob analysis to the frame to identify blob centroids within the frame; determining spatial co-location between each frame by clustering identified blob centroids across a time series of frames; determining statistics for the clustered blob centroids; aggregating the identified centroids into classes of clusters based on an analysis of the determined statistics for the clustered blob centroids; extracting one or more features associated with the classes of clusters; and determining the extracted one or more features represent movement or breathing of the target subject.

Additional example embodiments if the present invention may include one or more of the following features, methods, or functions. The received TOF data is captured by a TOF sensor proximate to the target subject. Parsing the TOF data to extract a phase frame and an amplitude frame from the TOF data includes extracting distance data from the phase frame and confidence data from the amplitude frame. Determining pixel velocities for pixels from distance data of the phase frame includes subtracting distance data extracted from a previous phase frame from distance data extracted from the phase frame. Down-selecting high confidence pixels using a mask generated from confidence data of the amplitude frame includes: identifying pixels that do not satisfy a threshold value for an associated amplitude; and/or nullifying the identified pixels using the mask generated from the confidence data. Filtering the high confidence pixels includes: applying a Gaussian low-pass filter to the high confidence pixels to spatially smooth the high confidence pixels; and/or performing temporal smoothing to select temporally correlated pixels of the high confidence pixels. After thresholding the filtered high confidence pixels, performing morphological erosion to identify relatively larger areas of movement within the frame. Performing blob analysis to the frame to identify blob centroids within the frame including: performing blob analysis to identify centroids of morphologically connected regions between frames; and aggregating the identified centroids of morphologically connected regions across all frames. Aggregating the identified centroids into classes of clusters based on an analysis of the determined statistics for the clustered blob centroids includes identifying the aggregated centroids using an iterated k-means algorithm. Determining the extracted one or more features represent movement or breathing of the target subject including: processing the extracted one or more features using a fuzzy controller; and/or classifying truth values output by the fuzzy controller using an artificial neural network to determine the extracted one or more features are associated with movement of the target subject or breathing of the target subject.

An additional example embodiment of the present invention includes a non-transitory computer-readable medium whose contents, when executed by a computing system, cause the computing system to perform a method for determining a movement status of a target subject, wherein the method comprises: receiving time of flight (TOF) data associated with a target subject; determining pixel velocities for pixels associated with one or more areas of the target subject; and determining whether the one or more areas of the target subject are moving based on the determined pixel velocities. The method may also comprise outputting a movement status for the target subject based on determining whether the one or more areas of the target subject are moving, wherein the movement status includes a status of movement of the target subject and a status of breathing of the target subject. And the method may further comprise receiving time of flight (TOF) data associated with a target subject includes receiving 3D TOF data from a TOF sensor that is proximate to the target subject and captures the 3D TOF data from the target subject. The method may additionally comprise of determining pixel velocities for pixels associated with one or more areas of the target subject including determining, for each pixel in a depth image of the target subject, a change in distance over time between depth frames of the depth image. And the method may still further comprise determining pixel velocities for pixels associated with one or more areas of the target subject includes filtering depth frames of a depth image of the target subject to identify pixel velocities associated with movement of the target subject.

In yet another example embodiment of the present invention a baby monitor configured to display images of a monitored baby comprises: a movement determination system configured to: access depth image data captured from images of the monitored baby; determine pixel velocities for pixels associated with one or more areas of the monitored baby; and determine whether the one or more areas of the monitored baby are moving based on the determined pixel velocities.

Further example embodiments of the present invention may include one or more of the following features. The movement determination system is further configured to: output a movement status for the monitored baby based on determining whether the one or more areas of the monitored baby are moving, wherein the movement status includes a status of movement of the monitored baby and a status of breathing of the monitored baby. The accessed depth image data associated with a monitored baby includes 3D time of flight (TOF) data captured by a TOF sensor of a capture device monitoring the baby and paired to a display device that displays the images of the monitored baby. The movement determination system determines pixel velocities by calculating, for each pixel in a depth image of the target subject, a change in distance over time between depth frames of the depth image. The baby monitor includes a capture device that captures the images of the monitored baby and contains the movement determination system.

Embodiments of the present invention may include one of the following advantages. A contactless method of monitoring and reporting a baby's well-being provides care givers with a peace of mind and potentially saves lives without the disadvantages of other sensor modalities such as wearables that can cause skin irritation, interrupt sleep, requires charging, and placing potentially hazard RF/batteries in close proximity or contact with the child. By having a wellness monitor integrated with a camera unit the installation is much easier then having to install and manage other hardware such as motion pads. Additionally, motion pads are of finite size and do not cover the entire sleeping surface resulting in false alarms. By having the wellness monitor integrated into the mounted camera, there is constant wall-powered supplied and end-users will not have to worry about the battery in a wearable dying. By integrating the wellness monitor into a camera monitor that is used by caregivers every day by default, the baby is monitored more often. Since wearables often require charging and purchasing additional clothing to house the sensor, they are quicker to abandon the wearable after some time and not to use it as frequently. By using a depth sensor such as TOF, RADAR or Ultrasound, there is greater immunity to noise compared to RGB-video processing based solutions which depend on pixel colors/contrast and can be adversely affected due to varying lighting conditions. Since the core signal processing is done locally on the camera unit, the system does not require expensive cloud hosting and processing which means end-users are not forced to pay monthly subscription fees. Monitoring breathing of a baby gives care-givers the quickest alert as to when a baby stops breathing. When a baby stops breathing, it takes time before the heart rate and SP02 readings of a wearable would reflect something is wrong. The topic invention alerts parents that something is wrong sooner than traditional heart rate and SP02 monitoring. In addition to apnea events, the system can also be used to alert care-givers if a child leaves their designated sleep area (e.g. gets out of bed/crib).

BRIEF DESCRIPTION OF THE DRAWINGS

Embodiments of the disclosed technology will be described and explained through the use of the accompanying drawings.

FIGS. 6A-6D are graphs illustrating pixel movement within images captured for an area of a target subject.

Figure 1:
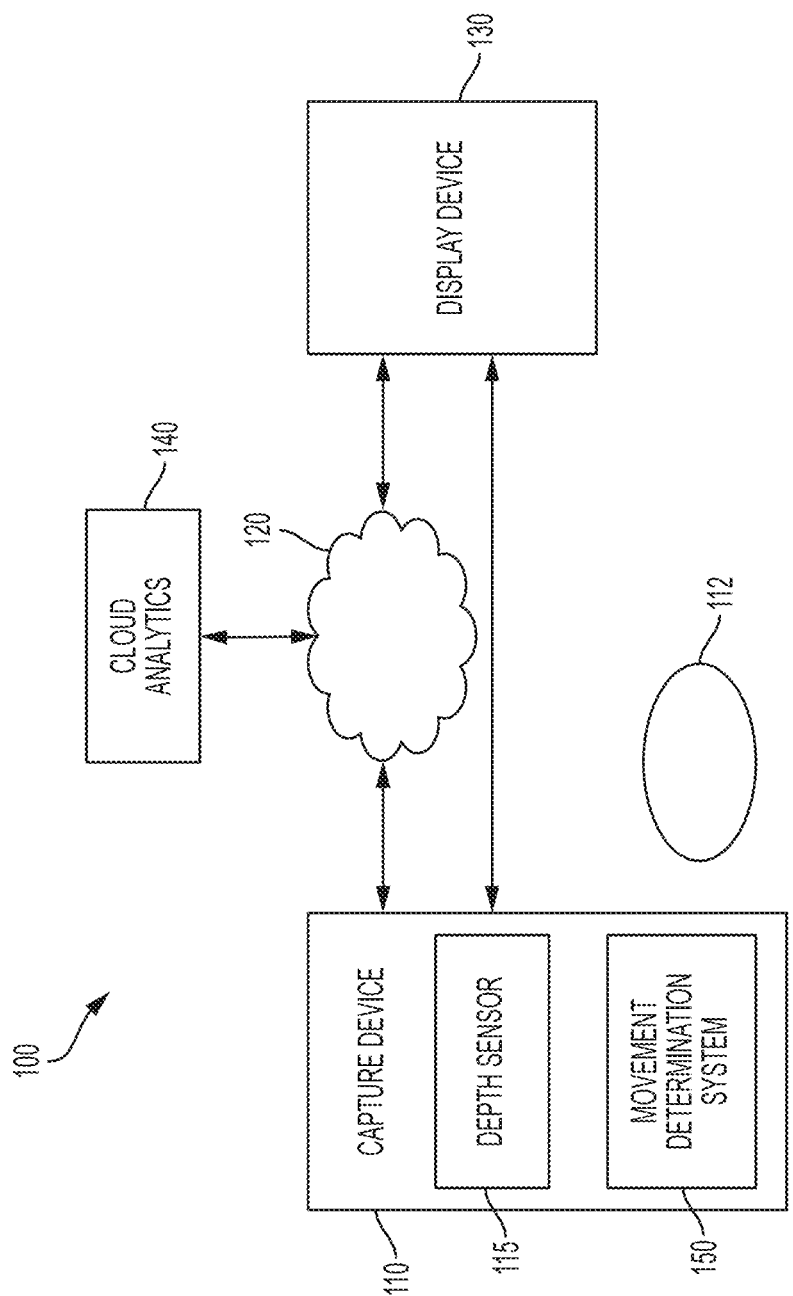
FIG. 1 is a block diagram illustrating a suitable computing environment for monitoring a baby or other target subject.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Overview

Systems and methods are described herein for monitoring and capturing information associated with target subjects, such as babies. For example, the systems and methods provide a capture device, such as a camera, that captures time of flight (TOF) data and/or other depth data (e.g., ultrasound) from a target subject. Using the depth data, the systems and methods, via a display device associated with (e.g., paired to) the capture device, present information about the target subject, such as information indicating movement of the target subject, information indicating a breathing rate of the target subject, information indicating a heart rate of the target subject, and so on.

Therefore, a baby monitor, which includes the systems and methods described herein, may present a video feed of a baby, captured by an associated camera, along with information that indicates the baby is moving and/or breathing at a certain rate. Using the information, the baby monitor, in some cases, may generate various status indicators and/or alerts that provide information regarding normal (e.g., the baby is breathing at a normal rate) or abnormal conditions (e.g., the baby has not moved in a specified time window).

In some embodiments, the systems and methods provide a capture device that monitors a baby, the capture device including one or more infrared light emitting devices (e.g. LEDs, IR laser with diffuser, and so on), an infrared sensor that captures infrared measurements for the monitored baby, and a time of flight (TOF) sensor that captures TOF data for the monitored baby.

Further, the systems and methods may provide a display device that displays a visual image of the monitored baby based on the data received from the capture device, the display device including a movement determination module that determines a state of movement of the monitored baby based on the TOF data for the monitored baby that is captured by the TOF sensor, and an indication module that causes the display device to present a first indicator associated with movement of the monitored baby and present a second indicator associated with breathing of the monitored baby.

For example, the systems and methods receive time of flight (TOF) data from a TOF sensor proximate to a target subject (captured by the capture device), and determine a movement status and breathing status of the target subject based on the received TOF data.

In some embodiments, the systems and methods determine a movement status of a target subject, by receiving time of flight (TOF) data associated with a target subject, determining pixel velocities for pixels associated with one or more areas of the target subject, and determining whether the one or more areas of the target subject are moving based on the determined pixel velocities.

For example, in order to extract the movement information from other captured movement information, the systems and methods receive time of flight (TOF) data measured from a target subject, parse the TOF data to extract a phase frame and an amplitude frame from the TOF data, determine pixel velocities for pixels from distance data of the phase frame, down-select high confidence pixels using a mask generated from confidence data of the amplitude frame, filter the high confidence pixels, threshold the filtered high confidence pixels, for each frame, perform blob analysis to the frame to identify blob centroids within the frame, determine spatial co-location between each frame by clustering identified blob centroids across a time series of frames, determine statistics for the clustered blob centroids, aggregate the identified centroids into classes of clusters based on an analysis of the determined statistics for the clustered blob centroids, extract one or more features associated with the classes of clusters, and determine the extracted one or more features represent movement or breathing of the target subject.

The systems and methods, therefore, capture time of flight (TOF) data from a target subject, such as a baby, in order to identify and measure specific current conditions or statuses of the baby, such as localized movement of the baby's body, breathing motions, heart rate, and so on. By using TOF data (and associated pixel velocities within images), which may be captured in low light or sunlit rooms or locations, a baby monitor may consistently and accurately track and capture vital information associated with the baby, providing parents and other caregivers with a robust and comprehensive view of their baby's physical status, among other benefits.

Various embodiments of the system will now be described. The following description provides specific details for a thorough understanding and an enabling description of these embodiments. One skilled in the art will understand, however, that the system may be practiced without many of these details. Additionally, some well-known structures or functions may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the invention.

Suitable Computing Environments

FIG. 1 is a block diagram illustrating a suitable computing environment 100 configured to monitor a baby or other target subject. A capture device 110 includes various components configured to capture information from a target subject 112, such as a baby sleeping or located in a crib, and/or process the captured data to determine movement information for the target subject 112.

The capture device 110 may include a video camera that captures multiple images of the baby, an infrared (IR) sensor that captures IR images of the baby, and a depth sensor 115, such as a time of flight (TOF) sensor that captures time of flight data from the baby, and so on. A display device 130 receives the data captured and processed by the capture device 110 over a network 120. The display device 130, which may be a standalone display and/or part of a computing device (such as a mobile device that run a mobile application associated with the capture device 110), communicates with the capture device 110 over various different networks 120, such as the Internet. The display device 130 and capture device 110 may also, in some embodiments, exchange information over various direct or peer-to-peer communication protocols (e.g., Wi-Fi, Bluetooth, and so on). Further, the display device 130 may receive data from multiple capture devices 110, such as two or more devices 110 that capture data associated with two or more babies 112.

A cloud analytics system 140 may store and/or perform analysis on various data captured by the capture device 110. For example, the display device 130, in determining whether to alert a parent of an abnormal condition, may utilize information provided by the capture device 110 along with previous information stored in the cloud system 140.

As described herein, in some embodiments, the capture device 110 processes the captured data (e.g., TOF or other depth data), in order to determine various movement characteristics for the target subject 112. The capture device 110, therefore, includes a movement determination system 150, which is configured to determine, based on data captured for the baby, whether the baby is moving, whether the baby is breathing (e.g., and associated rate of breathing), and other physiological parameters or measurements, such as the heart rate of the baby. The movement determination system 150 may include functional modules or systems that are implemented with a combination of software (e.g., executable instructions, or computer code) and hardware (e.g., at least a memory and processor). Accordingly, as used herein, in some examples a module or system is a processor-implemented module, system, or set of code and represents a computing device having a processor that is at least temporarily configured and/or programmed by executable instructions stored in memory to perform one or more of the particular functions that are described herein.

The system 150, for example, may include a metadata module that generates and sends metadata to the display device 110 that causes a user interface of the display device 130 to present a visual image of the monitored baby based on RGB data or infrared data captured by one or more image sensors of the capture device 110. For example, the system 150 may include a movement determination module that determines a state of movement of the monitored baby based on TOF data for the monitored baby that is captured by the TOF sensor of the capture device 110.

Although FIG. 1 depicts the movement determination system 150 as being part of the capture device 110, in some embodiments (not shown), aspects of the system 150 may reside and/or be performed by the display device 130 and/or the cloud analytics component 140. Further details regarding the capture device 110, the display device 130, and the movement determination system 150 are described herein.

Figure 2:
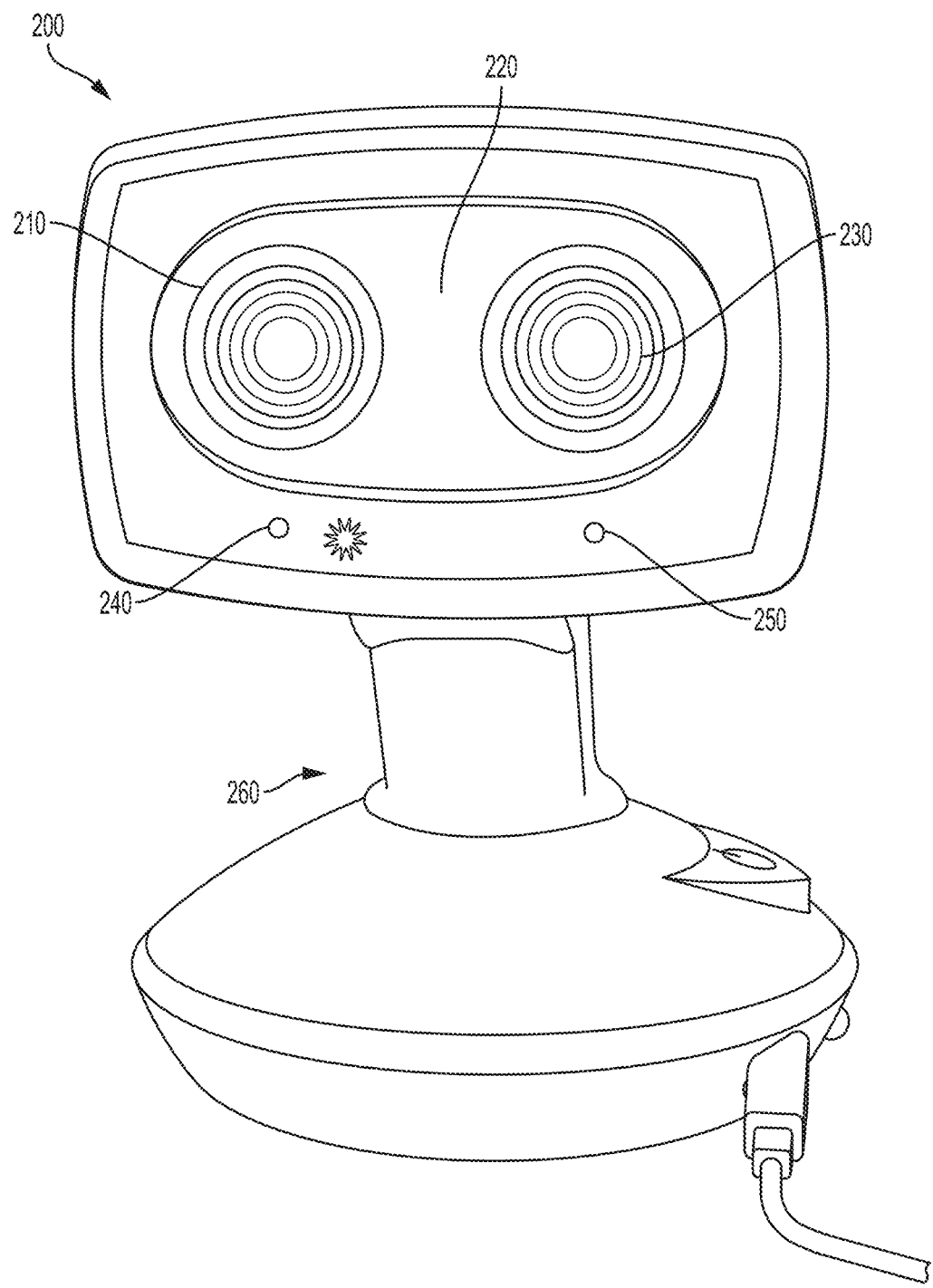
FIG. 2 is a diagram illustrating a capture device that captures information from a target subject.
Figure 3:
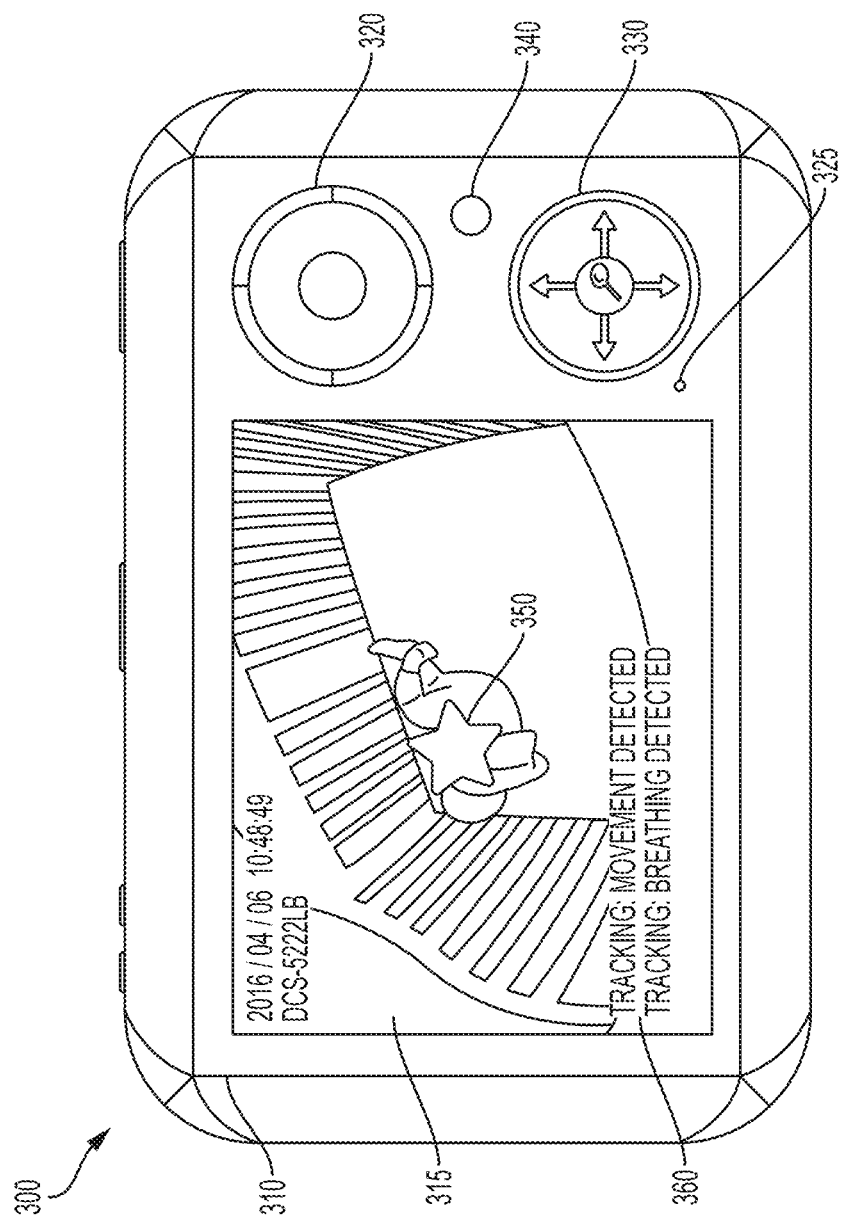
FIG. 3 is a diagram illustrating a display device that displays information captured from a target subject.

FIGS. 1-3 and the discussion herein provide a brief, general description of the components of the computing environment 100, the capture device 110, and/or the display device 130. Although not required, aspects of the computing environment 100, device 110, and/or device 130 are described in the general context of computer-executable instructions, such as routines executed by a general-purpose computer, e.g., mobile device, a server computer, or personal computer. The system can be practiced with other communications, data processing, or computer system configurations, including: Internet appliances, hand-held devices (including tablet computers and/or personal digital assistants (PDAs)), all manner of cellular or mobile phones, (e.g., smart phones), multi-processor systems, microprocessor-based or programmable consumer electronics, set-top boxes, network PCs, mini-computers, mainframe computers, and the like. Indeed, the terms "computer," "host," and "host computer," and "mobile device" and "handset" are generally used interchangeably herein, and refer to any of the above devices and systems, as well as any data processor.

Aspects of the environment 100 or devices 110, 130 can be embodied in a special purpose computing device or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communications network, such as a Local Area Network (LAN), Wide Area Network (WAN), or the Internet. In a distributed computing environment, program modules may be located in both local and remote memory storage devices.

Aspects of the environment 100 or devices 110, 130 may be stored or distributed on computer-readable media (e.g., physical and/or tangible non-transitory computer-readable storage media), including magnetically or optically readable computer discs, hard-wired or preprogrammed chips (e.g., EEPROM semiconductor chips), nanotechnology memory, or other data storage media. Indeed, computer implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Portions of the system reside on a server computer, while corresponding portions reside on a client computer such as a mobile or portable device, and thus, while certain hardware platforms are described herein, aspects of the system are equally applicable to nodes on a network. In an alternative embodiment, the mobile device or portable device may represent the server portion, while the server may represent the client portion.

In some embodiments, the devices 110, 130 may include network communication components that enable the devices to communicate with remote servers or other portable electronic devices by transmitting and receiving wireless signals using a licensed, semi-licensed, or unlicensed spectrum over communications network, such as the network 120. In some cases, the communication network 120 may be comprised of multiple networks, even multiple heterogeneous networks, such as one or more border networks, voice networks, broadband networks, service provider networks, Internet Service Provider (ISP) networks, and/or Public Switched Telephone Networks (PSTNs), interconnected via gateways operable to facilitate communications between and among the various networks.

Those skilled in the art will appreciate that various other components may be included in the devices 110, 130 to enable network communication. For example, the devices 110, 130 may be configured to communicate over a GSM or newer mobile telecommunications network. As a result, the devices 110, 130 may include a Subscriber Identity Module (SIM) card that stores an International Mobile Subscriber Identity (IMSI) number that is used to identify devices 110, 130 on the GSM mobile or other communications networks, for example, those employing LTE, 3G and/or 4G wireless protocols. If the devices 110, 130 are configured to communicate over another communications network, the devices 110, 130 may include other components that enable it to be identified on the other communications networks.

In some embodiments, the devices 110, 130 may include components that enable them to connect to a communications network using Generic Access Network (GAN), Unlicensed Mobile Access (UMA), or LTE-U standards and protocols. For example, the mobile device 110 may include components that support Internet Protocol (IP)-based communication over a Wireless Local Area Network (WLAN) and components that enable communication with the telecommunications network over the IP-based WLAN.

The communications network 120 may also include third-party communications networks such as a Global System for Mobile (GSM) mobile communications network, a code/time division multiple access (CDMA/TDMA) mobile communications network, a 3rd or 4th generation (3G/4G) mobile communications network (e.g., General Packet Radio Service (GPRS/EGPRS)), Enhanced Data rates for GSM Evolution (EDGE), Universal Mobile Telecommunications System (UMTS), Long Term Evolution (LTE) network), Voice over LTE (VoLTE) network, or other communications network. Further, the communications network 120 may include or be part of a wireless communications network, such as an Internet Multimedia System (IMS) network or other wireless networks.

Examples of Monitoring a Baby or Other Target Subject

As described herein, in some embodiments, the systems and methods capture TOF or other depth data from a monitored subject, which is then utilized to identify movement at various locations of the subject. FIG. 2 is a diagram illustrating a capture device 200 that captures information from a target subject and provides movement information to an associated display device.

The capture device 200 includes an RGB camera sensor 210 configured to capture RGB data (e.g., images and video) of the target subject, an IR light source 220 configured to illuminate the target subject with IR light, and a TOF camera sensor 230, which is configured to capture TOF data from the target subject.

The TOF sensor 230, which may be a 3D TOF camera sensor, operates by observing IR light (e.g., near-infrared range (~850 nm)) that is pulsed or modulated by a continuous-wave (CW), source (e.g., a sinusoid or square wave), which illuminates the target subject source. The target subject reflects the pulsed IR illumination. The TOF sensor 230 measures a phase shift between the illumination and the reflection, and translates the phase shift to a distance. Using the distance information, the TOF sensor 230 generates one or more depth frames, where each pixel in a depth frame represents the physical distance to various locations or areas at the target subject (e.g., in millimeters).

The capture device 200, therefore, may be a wireless video camera base station that includes one or more processors, a TOF depth sensor 230, an RGB camera 210, a light sensor 240, IR illumination LED's 220, mechanical IR cut filter, thermometer, a microphone 250, a speaker, PAN/TILT motors 260, an accelerometer, a proximity sensor, and at least one wireless transceiver.

In some cases, the capture device 200 is positioned to capture video and depth images from a sleeping area of a baby, such as via a stand or other apparatus configured to position the capture device 200 as a free-standing device, by mounting the device 200 to a crib and/or to other structures proximate to the crib, and so on.

As described herein, various different display devices may receive data from the capture device 200, such as TOF data, and present information that indicates various measured parameters or conditions associated with a baby or other target subject. FIG. 3 is a diagram illustrating a display device 300 that displays information captured from a target subject.

The display device 300, which may be a portable receiver device, such as a smartphone, tablet, or other custom receiving device, includes one or processors, a display 310, a speaker 320, a microphone 325, a visual indicator 340, various user controls 330, a battery, a wireless transceiver, and/or other components configured to display information, receive user input, present visual or audio information (e.g., alerts), and so on.

Via the display, the device 300 presents information 360 that is indicative of movement states of the target subject, which is determined by the TOF data received by the device 300. For example, the device 300 may display information 350 (e.g., icons or other visual indicators) that represents where a baby is moving, information that represents the baby is breathing, and so on.

Thus, in some embodiments, the capture device 200 uses the TOF sensor 230 to capture depth image data from a target subject to determine a state of movement of the monitored baby based on the depth image data for the monitored baby, and outputs movement information (e.g., certain metadata) to be transmitted to the display device 300. and Upon receiving the movement information, the display device 300 interprets the received metadata to extract the states of movement of the target subject 112, and presents various information representing the various states, such as a first indicator associated with movement of the monitored baby based on a determined state of movement of the monitored baby, and a second indicator associated with breathing of the monitored baby based on a determined state of movement of the monitored baby.

Figure 4:
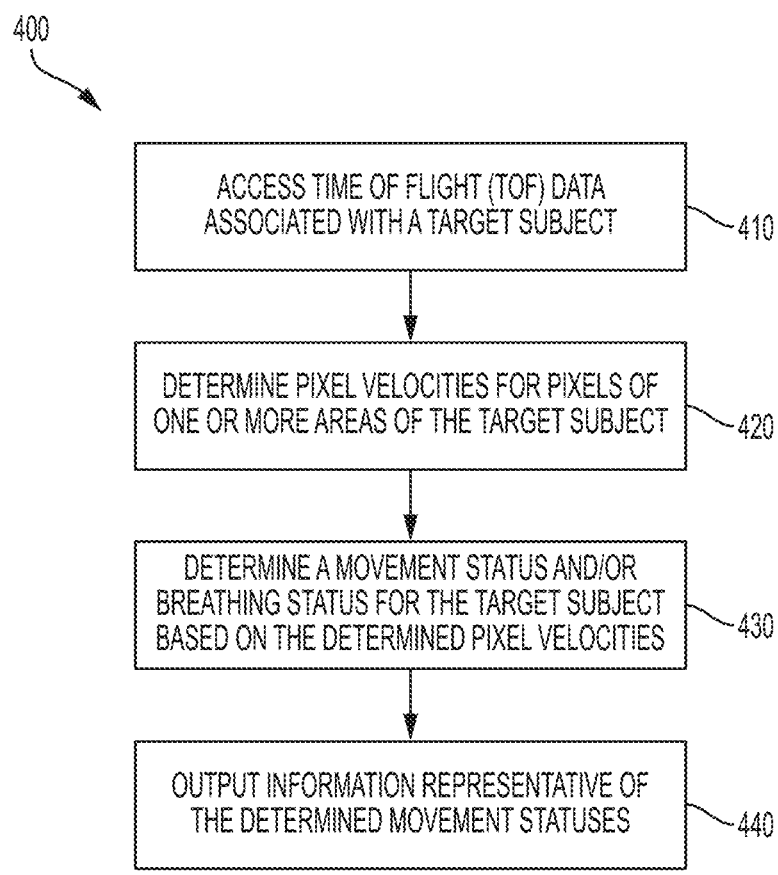
FIG. 4 is a flow diagram illustrating a method for displaying information captured from a monitored target subject.

FIG. 4 is a flow diagram illustrating a method 400 for displaying information captured from a monitored target subject. The method 400 may be performed by the movement determination system 150 and, accordingly, is described herein merely by way of reference thereto. It will be appreciated that the method 400 may be performed on any suitable hardware.

In operation 410, the system 150 receives time of flight (TOF) data associated with a target subject. For example, the system 150 may receive depth images (3D TOF data) captured by the TOF sensor 230 of the capture device 200, which is proximate to the target subject (e.g., a baby in a crib).

In operation 420, the system 150 determines pixel velocities for pixels associated with one or more areas of the target subject. For example, the system 150 determines, for each pixel in a depth image of the target subject, a change in distance over time between depth frames of the depth image. Thus, pixel velocity (Pv) is the change in distance (dR) over time between frames (dt) for each pixel in a depth image, or Pv=dR/dt. When a depth frame is returned in millimeters, the pixel velocity is calculated in units of millimeters per second (mm/s).

In operation 430, the system 150 determines whether the one or more areas of the target subject are moving based on the determined pixel velocities. FIGS. 5A-5D are images illustrating depth images (FIG. 5A) and associated pixel velocities (FIGS. 5B-D) for frames captured from a target subject.

Figure 5B:
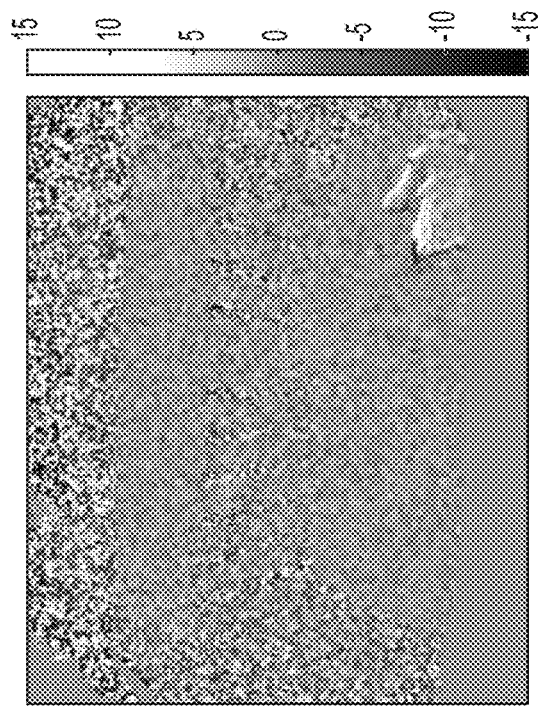
FIGS. 5A-5D are images illustrating depth images and associated pixel velocities for frames captured from a target subject.
Figure 5D:
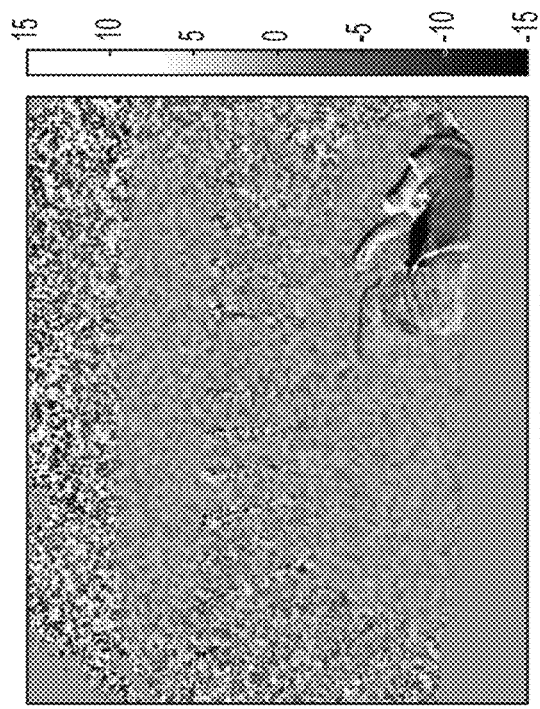
Figure 5A:
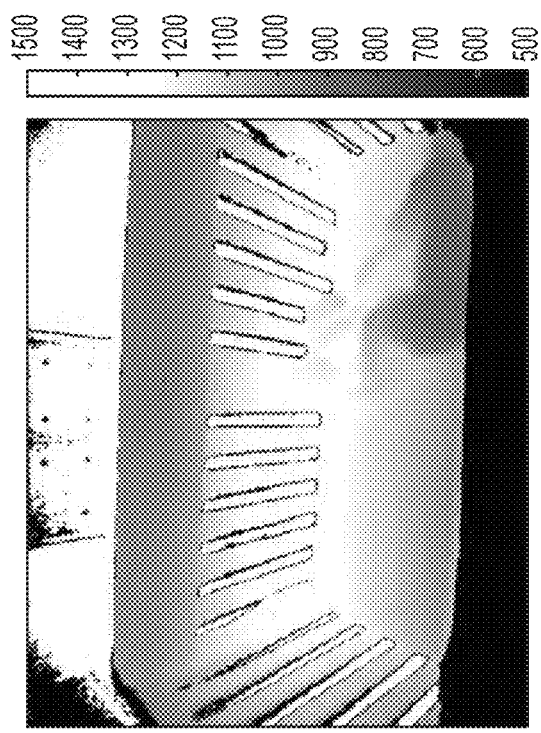

As shown in FIG. 5A, a sleeping baby is present in the lower right hand corner of the depth frame, and is about 900 mm (~3 feet) away from the camera. When looking at a high-definition RGB video, or the depth video of the sleeping baby, it will be difficult to detect the baby is breathing. However, using the calculated pixel velocities, the subtle breathing motions can be realized.

Figure 5C:
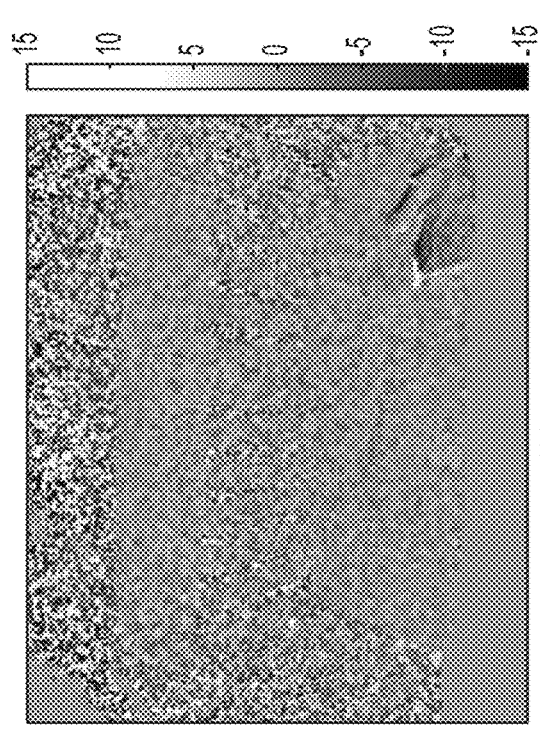

FIG. 5B shows the sleeping baby's torso expanding at around 5 mm per second, as the baby takes a breath in (which is well above a surrounding noise floor). FIG. 5C shows the sleeping baby's torso contracting at around −5 mm per second as the baby breathes out (which is well below the surrounding noise floor). Further, FIG. 5D shows the baby moving and re-adjusting in the crib, where the arms and legs of the baby are visible in the image (in addition to the breathing motion of the torso).

As described herein, FIGS. 5B-5D display a surrounding noise floor, which can be eliminated using spatial and temporal filtering. For example, the surrounding noise pixel velocities are extremely high frequency as compared to pixel velocities generated from a moving target, which enables the system 150 to filter the unwanted pixel velocities. Therefore, in some cases, the system 150 filters the depth frames of a depth image of the target subject to identify pixel velocities associated with movement of the target subject (described in greater detail herein).

FIGS. 6A-6D are graphs illustrating pixel movement within images captured for an area of a target subject, such as an analysis of single pixels over many pixel velocity frames (over time). FIG. 6A shows a single pixel found over a noisy region, where there is no motion by the baby. FIG. 6B shows a single pixel found over the torso of a sleeping (and breathing) baby. FIG. 6C shows the same pixel in FIG. 6A (no movement), after low-pass filtering has been applied. As depicted, the noise floor is effectively zero.

FIG. 6D shows the same pixel as FIG. 6B, after low-pass filtering has been applied. As depicted, the noise is effectively removed and the result is a clean respiratory signal. The system 150 may then calculate the respiration or breathing rate by taking a Fourier transform of the respiratory signal. Although not shown, the system 150 may perform a similar analysis to determine a heart rate, by monitoring subtle movements of the skin of the baby, caused by blood pumping in and out.

Figure 7:
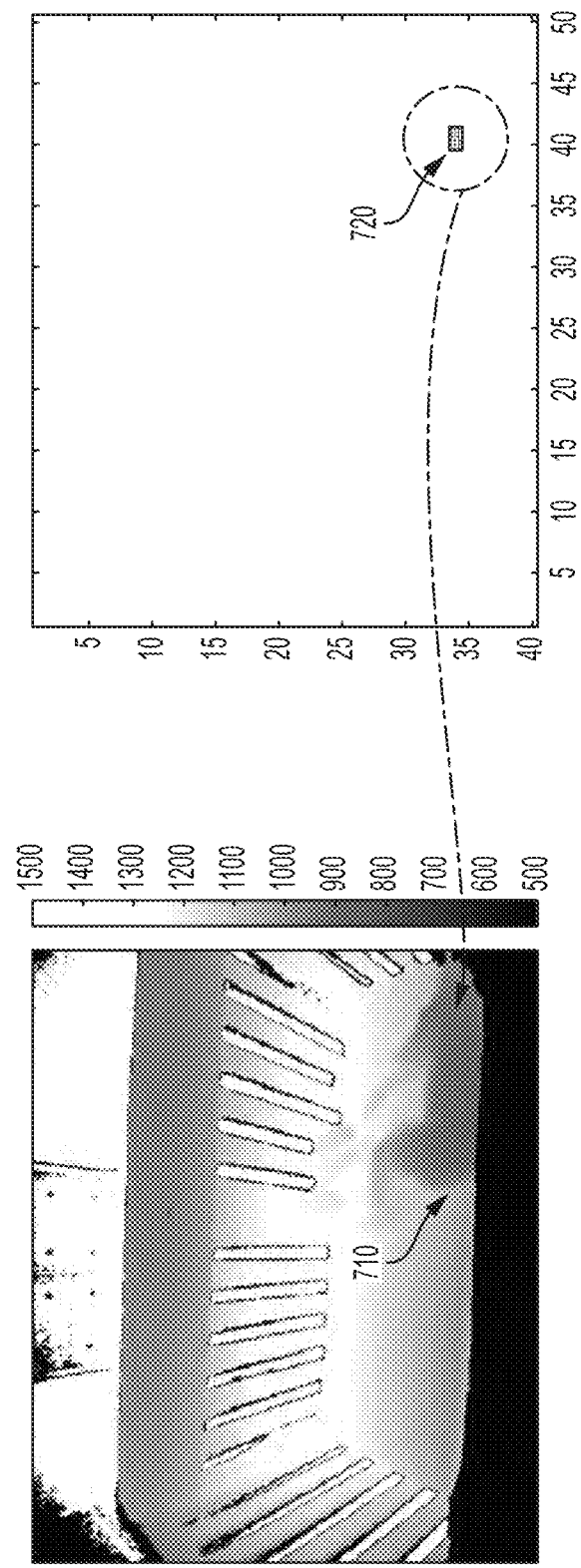
FIG. 7 is a diagram illustrating a mapping of a depth image to a binary motion matrix for a monitored target subject.

FIG. 7 is a diagram illustrating a mapping of a depth image to a binary motion matrix for a monitored target subject. Once low-pass filtering and spatial smoothing (averaging) techniques are applied to every pixel in the pixel velocity frame, along with dynamic thresholding, the system 150 may generate a Binary Motion Matrix. The Binary Motion Matrix represents areas in the image with true motion with a "1" and all background values to a "0". FIG. 7 depicts an example Binary Motion Matrix frame. As depicted, most of the areas represent zero motion, although area 720, which relates to the baby's movement 710 in the depth image, represents motion. The matrix, therefore, presents areas that map to movements of the baby in the depth image, such as breathing movements.

Referring back to FIG. 4, in operation 440, the system 150 outputs a movement status for the target subject based on determining whether the one or more areas of the target subject are moving, the movement status includes a status of movement of the target subject and a status of breathing of the target subject.

Once motion signals are determined, the system 150 classifies the motion signals as movement, breathing (rate) or no motion detected, and generates metadata associated with the classifications. For example, the system 150 may generate a classification of the motion signals (e.g., breathing and/or moving) along with the coordinates of where in the scene the motion is detected, among other information.

During classification, the system 150 performs frequency analysis over several frames to reveal if the motion is in a breathing range, uses clustering of motion detections and spatial size to distinguish between motion and breathing, and filters false signals (e.g., external factors) to isolate and identify the signals that represent breathing or other movement of the target subject.

As described herein, the display device 130, using the metadata classifications, may display or otherwise present the information in a variety of ways. The system 150 may present indicators on a visual image of the baby (e.g., icons or display elements that indicate areas in the image that are moving), and/or may present text or other indicators that present status information for the movement, breathing, and/or other monitored conditions of the baby.

The display device 300, therefore, may present information in a tracking mode. For example, parents may activate the tracking mode by long pressing a button located on the device 300, such as button 330. In tracking mode, the TOF sensor 230 provides the raw depth Image data (described herein) to a signal processor of the system 150 in the capture device 110, which determines return motion coordinate information (e.g., where in a scene the motion is occurring) and classification or movement status (e.g., baby breathing vs. baby moving).

Further, the system 150 may include alarm status counters that monitor time elapsed time periods between when moving/breathing events are detected. For example, if no breathing or movement has been detected for 5 seconds, the system 150 may set an "Alarm Status" as "Warning." If no breathing or movement has been detected for 15 seconds the system 150 may set the "Alarm Status" as "Alert," and present an alarm. Once breathing or motion detection resumes for 5 seconds, the system 150 may reset the "Alarm Status" to "Clear."

Thus, in tracking mode, a data payload is associated with RGB video frames. The data payload may include: Motion Coordinates [(X,Y) or NULL], Classification [Breathing, Moving or NULL], Alarm Status [Clear, Warning or Alert]. In presenting tracking information, the system 150 may display a marker overlaid over an image of a baby that pulsates as the baby breathes. As the baby moves around, a motion LED 340 provides status information. For example, when the baby is sleeping (e.g., is still and breathing) the motion LED 340 pulsates each time the baby takes a breath, and turns solid blue if they start to move around. If no motion (breathing or movement) is detected for 5 seconds, the motion LED 340 turns yellow. If no motion (breathing or movement) is detected for 15 seconds, the motion LED 340 turns red, and an audible alarms sounds until motion is detected again. Of course, the system 150 may utilize other indicator configurations or components.

Thus, in some embodiments, the systems and methods provides parents and other caregivers with various levels of information for a monitored baby. As described herein, the system 150 utilizes pixel velocity information from captured TOF data to identify and classify movement of the baby, which is output as various visual or multimedia indicators.

Examples of the Signal Processing Algorithm

The signal processing algorithm, as described herein, determines movement characteristics (e.g., subtle breathing motions) for a target subject within a monitored scene, such as a baby in a crib. Although the signal processing techniques with reference to TOF data, similar techniques may be employed with other depth data, such as radar data, acoustic data, ultrasonic data, and so on.

Figure 8:
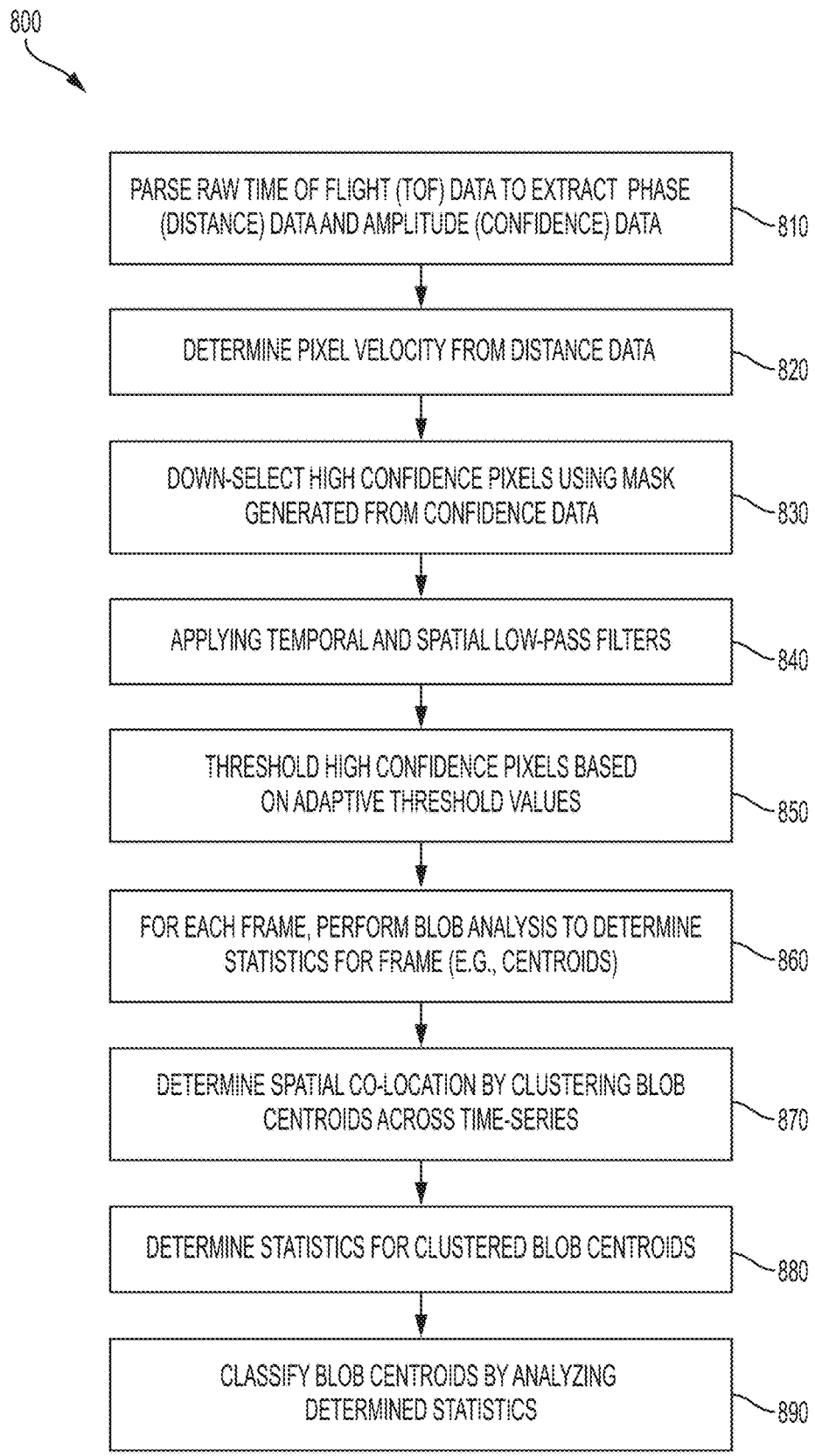
FIG. 8 is a flow diagram illustrating a method for determining movement and breathing for a monitored target subject.

FIG. 8 is a flow diagram illustrating a method for determining movement and breathing for a monitored target subject. The method 800 may be performed by the movement determination system 150 and, accordingly, is described herein merely by way of reference thereto. It will be appreciated that the method 800 may be performed on any suitable hardware.

In operation 810, the system 150 receives time of flight (TOF) data measured from a target subject and parses the TOF data to extract a phase frame and an amplitude frame from the TOF data. For example, the system 150 may receive raw TOF data captured by a TOF sensor proximate to the target subject, and extract distance data from the phase frame and confidence data from the amplitude frame.

In operation 820, the system 150 determines pixel velocities for pixels from distance data of the phase frame. For example, the system 150 subtracts distance data extracted from a previous phase frame from distance data extracted from the phase frame.

In operation 830, the system 150 down-selects high confidence pixels using a mask generated from confidence data of the amplitude frame. For example, the system 150 identifies pixels that do not satisfy a threshold value for an associated amplitude, and nullifies the identified pixels using the mask generated from the confidence data.

In operation 840, the system 150 filters the high confidence pixels by applying temporal and spatial low-pass filters. For example, the system 150 applies a Gaussian low-pass filter to the high confidence pixels to spatially smooth the high confidence pixels, and performs temporal smoothing to select temporally correlated pixels of the high confidence pixels.

In operation 850, the system 150 thresholds the filtered high confidence pixels. After thresholding, the system 150 may perform morphological erosion to identify relatively larger areas of movement within the frame.

In operation 860, the system 150, for each frame, performs blob analysis to the frame to identify blob centroids within the frame. For example, the system 150 performs blob analysis to identify centroids of morphologically connected regions between frames, and aggregates the identified centroids of morphologically connected regions across all frames.

In operation 870, the system 150 determines spatial co-location between each frame by clustering identified blob centroids across a time series of frames, and, in operation 880, determines statistics for the clustered blob centroids.

In operation 890, the system 150 aggregates the identified centroids into classes of clusters based on an analysis of the determined statistics for the clustered blob centroids, extracts one or more features associated with the classes of clusters, and determines the extracted one or more features represent movement or breathing of the target subject. For example, the system 150 may identify the aggregated centroids using an iterated k-means algorithm, process the extracted one or more features using a fuzzy controller, and classify truth values output by the fuzzy controller using an artificial neural network to determine the extracted one or more features are associated with movement of the target subject or breathing of the target subject.

Figure 9:
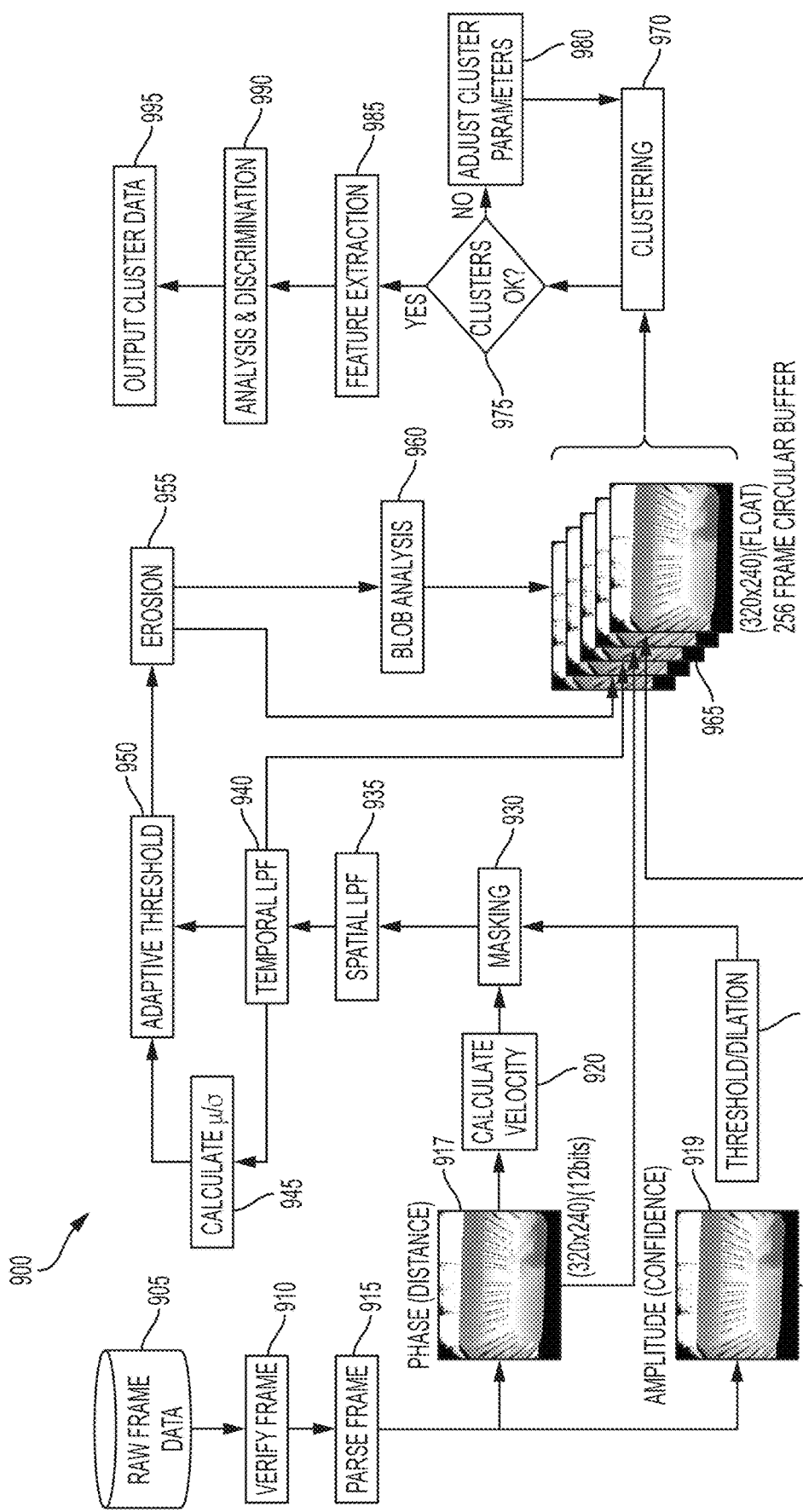
FIG. 9 is a flow diagram illustrating a method for processing signals received from a capture device that is monitoring a target subject.

The system 150, therefore, applies various signal processing and data analysis techniques to depth image data to isolate and/or focus on pixel velocities derived from TOF data that represent subtle motions of a baby. FIG. 9 is a flow diagram illustrating a method 900 for processing signals received from a capture device that is monitoring a target subject. The method 900 may be performed by the movement determination system 150 and, accordingly, is described herein merely by way of reference thereto. It will be appreciated that the method 900 may be performed on any suitable hardware.

The system 150, in operation 905, receives raw frame data, such as 320×240 depth frames in mm (16 bits of resolution), 320×240 Confidence data grey scale (16 bits of resolution), and associated time stamps. In operation 910, the system 150 verifies the data, and in operation 915, parses the data to extract phase frames 917 (e.g., distance) and amplitude frames 919 (e.g., confidence), which are placed into a next position of a circular buffer (256-frame circular buffer).

In operation 920, using the distance frame 917, the system 150 calculates pixel velocity by subtracting phase information (distance) from frame $N-N_0$ from the current frame 917. In operation 930, the system 150 applies masking to the calculated pixel velocities. The system 150, in operation 925, sets a threshold value to discriminate low amplitude (e.g., low confidence) pixels, generates a mask, and uses the mask to the calculated pixel velocities to nullify phase (e.g., distance) pixels with low confidence measurements.

In operation 935, the system 150 applies spatial smoothing to the high confidence pixels. For example, because multiple pixels of a target subject will exhibit similar velocity characteristics, a spatial low-pass filter attenuates otherwise high intensity noise. The system 150, therefore, may apply one or more spatial low-pass filters to realize spatial smoothing, using filter kernels such as Gaussian, Uniform cony. Kernel, Median filter, and so on.

In operation 940, the system 150 performs temporal smoothing to the high confidence pixels. For example, due to known oversampling (e.g., 30 Hz framerate vs 1 Hz respiration), the system 150 may exhibit consistent velocity characteristics over time. The system 150 may use temporal smoothing to select only temporally correlated data from uncorrelated noise, where a weighted filter places highest priority on current frame (e.g., reduction in latency).

In operation 945, the system 150 calculates the frame mean and standard deviation, which, in operation 950, is utilized to dynamically threshold the pixel data. In operation 955, the system 955 applies morphological erosion, which removes salt and pepper noise and locations of movement with insufficient area (e.g., a twitching toe), resulting in larger areas of motion (e.g., baby's relatively large torso) remaining.

In operation 960, the system 150 performs blob analysis, where centroids of morphologically connected regions are identified, and centroids are aggregated over all frames in the buffer.

Using the 256-frame circular buffer of frames 965, the system 150, in operation 970, clusters the frame centroids, where aggregated centroids are identified using an iterated k-means algorithm, which, in operation 975, determines whether the clusters are sufficient, and, in operation 980, adjusts the clusters.

In operation 985, the system 150 extracts features from the clusters, and, in operation 990, analyzes the temporal and spatial characteristics of clusters, using frequency and area characteristics to discriminate classes of clusters. For example, the system 150 utilizes the features to discriminate classes of clusters using Neuro-Fuzzy control, where inputs are processed by a fuzzy controller to map statistical outputs to membership functions and truth values.

In operation 995, the system 150, inputs the truth values as input to an artificial neural network (ANN), which classifies the inputs as various movement states or statuses, such as movement/breathing/no baby activity (e.g., along with alarm status). For example, as described herein, the system 150 may output the ANN status information as an overlay onto a high resolution RGB video feed of baby in real time.

Thus, in some embodiments, the system 150 applies various signal processing and data analysis techniques to depth image data to isolate and/or focus on pixel velocities derived from TOF data that represent subtle motions of a baby, such as motions associated with a baby breathing (e.g., motions of the baby's torso), the baby's heart rate (e.g., motions of the baby's skin), and so on.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims

We claim:

1. A method of detecting body movement status and body breathing status in a target subject, said method comprising the steps of:

receiving time of flight (TOF) data measured from said target subject;

parsing the TOF data to extract a phase frame and an amplitude frame from the TOF data;

extracting distance data for pixels from said phase frame, and extracting confidence data for said pixels from said amplitude frame;

determining pixel velocities for said pixels using said distance data of said phase frame;

masking said pixels to nullify any of said pixels below a selected amplitude threshold, therein producing high confidence pixels, wherein masking is performed using a mask generated from said confidence data of said amplitude frame;

filtering said high confidence pixels to produce filtered high confidence pixels;

thresholding said filtered high confidence pixels to identify areas of movement in a time series of frames;

performing blob analysis to identify blob centroids within said time series of frames;

determining spatial co-location by clustering said blob centroids that were identified across a said time series of frames;

determining statistics for said blob centroids that were identified;

aggregating said blob centroids that were identified into classes of clusters based on an analysis of said statistics, wherein said classes of clusters include a first class representative of said body movement status and a second class representative of said body breathing status;

extracting said body movement status and said body breathing status from said classes of clusters.

2. The method of claim 1, wherein said TOF data received is captured by a TOF sensor proximate to the said target subject.

3. The method of claim 1, wherein determining pixel velocities includes subtracting distance data extracted from a previous first phase frame from distance data extracted from a second phase frame.

4. The method of claim 1, wherein filtering said high confidence pixels includes: applying a Gaussian low-pass filter to said high confidence pixels to spatially smooth said high confidence pixels; and performing temporal smoothing to select temporally correlated pixels of said high confidence pixels.

5. The method of claim 1, further comprising: after thresholding said filtered high confidence pixels, performing morphological erosion to identify relatively larger areas of movement within said time series of frames.

6. The method of claim 1, wherein performing blob analysis to identify blob centroids within said time series of frames includes:

performing blob analysis to identify centroids of morphologically connected regions between frames in said time series of frames; and aggregating said centroids of morphologically connected regions identified across said time series of frames.

7. The method of claim 1, wherein aggregating said blob centroids into classes of clusters based on an analysis of said statistics includes identifying said aggregated centroids using an iterated k-means algorithm.

8. The method of claim 1, wherein extracting said body movement status and said body breathing status from said classes of clusters includes: processing using a fuzzy controller; and classifying truth values output by said fuzzy controller using an artificial neural network to determine said body movement status and said body breathing status.

* * * * *